United States Patent

Gschwender et al.

[11] Patent Number: 5,302,760
[45] Date of Patent: Apr. 12, 1994

[54] STABILITY ADDITIVE FOR PERFLUOROPOLYALKYLETHERS

[75] Inventors: Lois J. Gschwender, Kettering; Carl E. Snyder, Jr., Trotwood, both of Ohio

[73] Assignee: The United States of America as represented by the Secretary of the Air Force, Washington, D.C.

[21] Appl. No.: 30,969

[22] Filed: Mar. 12, 1993

[51] Int. Cl.$^5$ ............................................. C07C 41/46
[52] U.S. Cl. ..................... 568/581; 568/637; 568/639
[58] Field of Search ..................... 508/581, 639, 637

[56] References Cited

U.S. PATENT DOCUMENTS

| | | | |
|---|---|---|---|
| 2,547,679 | 4/1951 | Wolfe | 568/639 |
| 3,376,350 | 4/1968 | Wen | 568/639 |
| 3,576,882 | 4/1971 | Clark | 568/639 |
| 3,760,003 | 9/1973 | Asadorian et al. | 568/637 |
| 4,097,388 | 6/1978 | Snyder et al. | 252/49.9 |
| 4,172,959 | 10/1979 | Kaiser | 568/637 |
| 4,174,461 | 11/1979 | Sianesi et al. | 568/582 |
| 4,981,727 | 1/1991 | Brinduse et al. | 427/385.5 |
| 5,000,864 | 3/1991 | Strepparola et al. | 252/51.5 |

FOREIGN PATENT DOCUMENTS 2-59531  2/1990  Japan ................... 568/639

*Primary Examiner*—James H. Reamer
*Attorney, Agent, or Firm*—Charles E. Bricker; Thomas L. Kundert

[57] ABSTRACT

Stability enhancing additives of the formula:

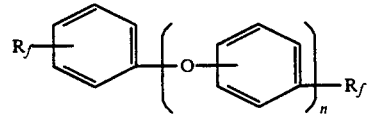

where $R_f$ is a perfluoroalkyl group having 1 to 15 carbon atoms and n has a value of 1 to 6, for perfluoropolyalkylether fluids. These additives are incorporated into perfluoropolyalkylether fluids in an amount ranging from about 0.01 to 3 weight percent.

6 Claims, No Drawings

STABILITY ADDITIVE FOR PERFLUOROPOLYALKYLETHERS

RIGHTS OF THE GOVERNMENT

The invention described herein may be manufactured and used by or for the Government of the United States for all governmental purposes without the payment of any royalty.

BACKGROUND OF THE INVENTION

This invention relates to stability additives for perfluoropolyalkylether fluids.

Highly fluorinated compounds have long been of interest because of their excellent potential for high temperature applications. Fluids based on perfluoropolyalkylethers (PFPAE) have, in addition to high thermal and oxidative stability, a wide liquid range which make them ideal candidates for aerospace applications. These fluids consist essentially of a mixture of fluorinated polyethers. These fluids have the general formula:

$$R_fO(Z)_m(Y)_nR_f$$

wherein $R_f$ is a lower perfluoroalkyl group, such as $CF_3$, $C_2F_5$, $C_3F_7$ and the like, wherein Z is $-CX_2CX_2O-$, $-CX_2CX_2CX_2O-$ or $-CX_2OCX_2CX_2O-$, where X is $-F$, $-CF_3$, $-C_2F_5$ and the like, and Y is $-CFXO-$, m and n are integers whose sum is between 2 and 200 and the ratio of n to m is between 0.1 and 10, and wherein the Z and Y units are statistically distributed along the PFPAE chain. Commercial base fluids of this type have been available for some time, for example, Krytox ® (DuPont), Fomblin ® (Ausimont), Demnum ® (Daikin) and the like. Their practical utility in aerospace and military applications has been hampered by the wear and corrosion of certain metal components exposed to these base fluids under extreme conditions.

Deficiencies in base fluids are generally removed and the performance of the fluids improved by the use of additives. Conventional additives developed for the improvement of a variety of specific properties of hydrocarbon base fluids are generally not suitable for perfluorinated fluids. These conventional additives are not soluble in perfluorinated fluids and are ineffective. One way of overcoming this incompatibility is to synthesize compounds containing fluoroalkylether groups plus selected functional groups for specific activity. Although this approach may make the compound soluble in a fluorinated base fluid, mere replacement of hydrocarbon groups with fluorocarbon groups can change the useful properties of the additive itself by changing the properties of the critical functional group present in the additive. These difficulties are well known to those familiar with the art. In spite of these difficulties, a few useful additives have been developed for perfluorinated fluids. One such example is the development of PFAE substituted triphenylphosphines, C. E. Snyder, Jr. and C. Tamborski, U.S. Pat. No. 4,097,388. These additives, when dissolved in PFPAE fluids, have significantly reduced the corrosion of certain metal components exposed to the fluid at high temperatures in an oxidative environment.

We have discovered a group of compounds which do not contain fluoroalkylether groups, yet are soluble in fluorinated base fluids. These compounds enhance the stability of fluorinated base fluids.

Accordingly, it is an object of this invention to provide novel stability enhancing additives for perfluoropolyalkylethers.

Another object of this invention is to provide perfluorinated fluids having improved stability properties.

Other objects and advantages of the invention will be apparent to those skilled in the art.

SUMMARY OF THE INVENTION

In accordance with the present invention, there are provided phenyl ethers substituted with perfluoroalkyl substituents, of the following general formula:

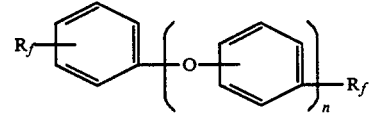

where $R_f$ is a perfluoroalkyl group having 1 to 15 carbon atoms and n has a value of 1 to 6. $R_f$ may be branched or unbranched.

The di-substituted phenyl ether may be prepared by coupling a dihaloaromatic ether

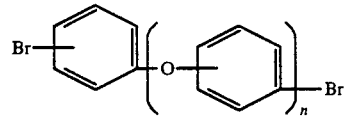

with a fluorinated alkyl iodide, $C_mF_{2m+1}I$, wherein m is 1 to 15, in a suitable solvent in the presence of copper bronze powder, under suitable reaction contidions. Suitable solvents include dimethyl sulfoxide, N,N-dimethylformamide, sulfolane and the like. The reaction is, in general, exothermic. Accordingly, it is necessary to carry out the reaction in a controlled manner, such as by controlling the rate of addition of one reactant to the other or by cooling the reaction vessel, or both. Reaction progress can be monitored by periodic sampling of the reaction mixture.

The bis-perfluoroalkyl phenyl ethers of this invention are mixed with perfluoropolyalkylether fluids in an amount ranging from 0.01 to 3.00 weight percent to provide fluids having enhanced stability.

The following examples illustrate the invention:

EXAMPLE I

Synthesis of 4,4'-bis(perfluoro-n-hexyl)diphenyl ether 21.4 g (48 mmol) of n-$C_6F_{13}I$ was added dropwise to a stirred mixture of 6.72 g (106 mmol) copper bronze powder, 6.56 g (20 mmol) 4,4'-dibromodiphenyl ether and 60 ml dimethylsulfoxide at about 125° C. over a period of about 50 minutes. The reaction was exothermic, so the rate of addition was controlled so that the reaction temperature did not exceed 135° C. Periodic aliquot samples were removed, hydrolyzed and analyzed by gas chromatography. After stirring at 120° C. for 5 hours, the yield of expected product was maximized. The reaction mixture was cooled to room temperature, and 100 ml diethyl ether and 50 ml water were added thereto. The mixture was stirred, then centrifuged. The ether and water layers were decanted from the solid materials and separated. The solid was extracted with additional diethyl ether (2×50 ml). The ether solutions were combined, washed with two 80 ml portions of distilled water, then dried over anhydrous MgSO$_4$. 14.3 g (97 GC area %) of crude product was obtained from evaporation of the solvent. The crude product was distilled to yield 12.7 g (79% yield) of 4,4'-bis(perfluoro-n-hexyl)diphenyl ether, bp 138°–140° C./0.45 mm, mp 58°–59° C.

EXAMPLE II

One and two percent (w/w) formulations of 4,4'-bis(-perfluoro-n-hexyl)diphenyl ether in Fomblin Z, a linear PFPAE available commercially from Ausimont, Inc. Morristown, N.J., was prepared. Micro corrosion oxidation tests were performed using these formulations with steel coupons, at 288°, 315° and 345° C. Briefly, dry air is bubbled through 20 ml of fluid for 24 hours at a rate of one liter per hour at a specific temperature. The test is performed in the overboard configuration with the air and gasses from the test vented to the outside, as opposed to passing through a reflux condenser. Steel alloy coupons, as listed in the table, separated by glass spacers, are stacked in the fluid and serve to catalyze fluid degradation. At the end of the test, fluid property changes and metal weight changes are determined. Results of the test are shown in the following table:

TABLE I

| Measured Properties | Base Oil (288° C.) | Base Oil + 1% add. (288° C.) | Base Oil + 1% add. (316° C.) | Base Oil + 2% add. (345° C.) |
|---|---|---|---|---|
| % Visc. Chg. (40° C.) | −95.60 | 0.80 | 1.80 | 0.90 |
| Acid NR mg KOH/gm | 10.10 | 0.00 | 0.00 | 0.00 |
| Fluid Wt. Loss, % | 49.50 | 0.00 | 0.40 | 0.30 |
| Metal Wt. Chg (mg/cm$^2$) | | | | |
| 4140 | 0.00 | 0.00 | 0.31 | 0.29 |
| 52100 | 0.16 | 0.04 | 0.07 | 0.37 |
| 410 | −0.14 | −0.04 | 0.11 | −0.06 |
| M50 | 0.72 | 0.06 | 0.27 | −0.38 |
| 440C | 0.58 | 0.06 | 0.17 | −0.11 |

EXAMPLE III

A one percent (w/w) formulation of 4,4'-bis(perfluoro-n-hexyl)diphenyl ether in Krytox 143AC, a branched PFPAE available commercially from E.I. duPont de Nemours, Inc., Wilmington, Del., was prepared. Micro corrosion oxidation tests were performed using this formulation with steel coupons at 316° and 343° C. Results of these test are shown in the following table:

TABLE II

| Measured Properties | Base Oil (316° C.) | Base Oil + additive (316° C.) | Base Oil + additive (343° C.) |
|---|---|---|---|
| % Visc. Chg. (40° C.) | 1.60 | 2.41 | 3.30 |
| Acid NR mg KOH/gm | 0.05 | 0.00 | 0.05 |
| Fluid Wt. Loss, % | 10.06 | 0.28 | 0.30 |
| Metal Wt. Chg (mg/cm$^2$) | | | |
| 4140 | 2.06 | 0.00 | −0.03 |
| 52100 | 1.06 | −0.04 | 0.10 |
| 410 | −4.20 | −0.02 | −0.12 |
| M50 | 0.04 | 0.02 | −0.50 |
| 440C | −2.78 | 0.02 | −0.58 |

EXAMPLE IV 1,3-bis(3-perfluoro-n-heptyl phenoxy) benzene was synthesized following the procedure given in Example I. Micro corrosion tests were performed following the procedure given in Example II. For these tests, fluid volume was reduced to 6 ml and the apparatus was miniaturized. The results of these tests are given in the following table:

TABLE III

| Measured Properties | Base Oil (260° C.) | Base Oil + 1% add. (315° C.) |
|---|---|---|
| % Visc. Chg. (40° C.) | −41.95 | 1.85 |
| Fluid Wt. Loss, % | 26.95 | 0.00 |
| Metal Wt. Chg (mg/cm$^2$) | | |
| 4140 | 0.43 | 0.11 |
| 52100 | −0.18 | 0.15 |
| 410 | −2.67 | 0.00 |
| M50 | −0.16 | 0.10 |
| 440C | −2.68 | 0.06 |

It can be seen from the tables that the bis-perfluoroalkyl phenyl ethers of this invention improve the base oil fluid/metal corrosion properties.

Various modifications may be made to the invention as described without departing from the spirit of the invention or the scope of the appended claims.

We claim:

1. A perfluorinated fluid having improved stability consisting essentially of a perfluoropolyalkylether and about 0.01 to 3.0 weight percent of a bis-perfluoroalkyl phenyl ether of the formula:

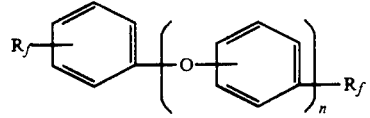

where R$_f$ is a perfluoroalkyl group having 1 to 15 carbon atoms and n has a value of 1 to 6.

2. The fluid of claim 1 containing about 1.0 weight percent 4,4'-bis(perfluoro-n-hexyl)diphenyl ether, balance a linear perfluoropolyalkylether.

3. The fluid of claim 1 containing about 2.0 weight percent 4,4'-bis(perfluoro-n-hexyl)diphenyl ether, balance a linear perfluoropolyalkylether.

4. The fluid of claim 1 containing about 1.0 weight percent 4,4'-bis(perfluoro-n-hexyl)diphenyl ether, balance a branched perfluoropolyalkylether.

5. The fluid of claim 1 containing about 1.0 weight percent 1,3-bis(3-perfluoro-n-heptyl phenoxy) benzene, balance a linear perfluoropolyalkylether.

6. A bis-perfluoroalkyl phenyl ether of the formula:

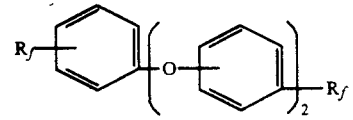

where R$_f$ is n-C$_7$F$_{15}$.

* * * * *

UNITED STATES PATENT AND TRADEMARK OFFICE
CERTIFICATE OF CORRECTION

PATENT NO. : 5,302,760
DATED : April 12, 1994
INVENTOR(S) : Lois J. Gschwender, et. al.

It is certified that error appears in the above-indentified patent and that said Letters Patent is hereby corrected as shown below:

Column 4, line 46, "6" should be -- 2 --.

Signed and Sealed this

Twentieth Day of September, 1994

Attest:

BRUCE LEHMAN

*Attesting Officer*     *Commissioner of Patents and Trademarks*